United States Patent [19]

Santini

[11] Patent Number: 4,809,912

[45] Date of Patent: Mar. 7, 1989

[54] MEMBRANE-GEL DIFFUSION DEVICE

[75] Inventor: Thomas F. Santini, Allentown, N.J.

[73] Assignee: deLaire, Inc., New York, N.Y.

[21] Appl. No.: 32,047

[22] Filed: Mar. 27, 1987

[51] Int. Cl.4 ............................................. A61L 9/04
[52] U.S. Cl. ....................................... 239/60; 239/57; 424/76.1
[58] Field of Search .................. 239/54, 55, 56, 60; 424/76

[56] References Cited

U.S. PATENT DOCUMENTS

| | | | |
|---|---|---|---|
| 3,985,298 | 10/1976 | Nichols | 239/54 |
| 4,157,787 | 6/1979 | Schwartz | 239/60 |
| 4,161,283 | 7/1979 | Hyman | 239/55 |
| 4,248,380 | 2/1981 | Lee et al. | 239/53 |
| 4,356,969 | 11/1982 | Obermayer et al. | 239/60 |
| 4,399,942 | 8/1983 | Chand | 239/34 |
| 4,634,614 | 1/1987 | Holzner | 239/55 |
| 4,755,377 | 7/1988 | Steer | 424/76.4 |

FOREIGN PATENT DOCUMENTS 1517410 7/1978 United Kingdom .

*Primary Examiner*—Andres Kashnikow
*Assistant Examiner*—Chris Trainor
*Attorney, Agent, or Firm*—Hayes, Soloway, Hennessey & Hage

[57] ABSTRACT

A method for the fabrication of a continuous action reservoir type air freshening device is described. The device is characterized by the use of an evaporation rate controlling porous membrane which is in intimate contact and completely covers the exposed surface of an erodible gel-type of solid perfume composition. The fragranced gel is enclosed in a container, one end of which is open and over which is affixed the porous membrane. One side of this membrane is exposed to the atmosphere; the other side intimately contacts the solid reservoir consisting of the fragrance gel. Transmission of the volatile fragrance and carrier agents to the surrounding environment through the porous membrane matrix occurs as a function of an evaporative process. The membrane permits only a limited penetration, if any by the gel solution, i.e. in the liquid state, but is sufficiently permeable to the gel solution to establish physical attachment between the solidified gel and the membrane.

45 Claims, 2 Drawing Sheets

MEMBRANE-GEL DIFFUSION DEVICE

The present invention relates to dispersing devices and more particularly to dispersing devices for the controlled release of air treating materials from a device which utilizes a gel reservoir. The invention has particular application for use with so-called continuous action air freshening units and will be described in connection with such application although other applications are contemplated.

The controlled dispensing of fragrance and the capacity to create an odor impression in a substantially closed space is the primary concern of all the methodologies which have addressed the area of air freshening and fragrance diffusion. The importance of a controlled release not only manifests itself from the point of view of fragrance selection, but also proves to be important when concern over the functional life of the unit is considered. Economically viable devices must be efficient in their performance due to high costs often associated with fragrance. Premature release of the fragrance not only creates a potential for excess odor production in the early stages of the product's functional life, but also diminishes the reservoir of fragrance which can be drawn upon in the latter stages of the performance life of the device. Diffusion methodologies are frequently compared over a given time frame with identical loadings of fragrance so that critical, controlled evaluations may be made with regard to odor intensity and product longevity. Superior technologies will be those that are able to produce a greater odor impression over a longer period for a given fragrance loading than similarly intended methodologies.

Solid compositions in which a fragrance or perfume is dispersed within a matrix formed by a gelling agent offer a particularly desirable and relatively low cost commercial delivery method for continuous action fragrance release devices. Gels can commonly range from being very soft solids to what is termed "ringing gels", which have greater mechanical integrity. The topic of gel formulation has been covered in extensive detail in *Cosmetics and Toiletries*, November 1984, Allured Publishing, pages 19-55 to include such gelling agents as:

(A) Synthetic gums and resins—methylcellulose, polyethylene glycol;
(B) Natural gums—carrageenan, tragacanth gum, locust-bean gum and guar;
(C) Inorganic materials—expandable clays;
(D) Higher molecular weight polyethylenes and co-polymers;
(E) Metallic soaps—aluminum, sodium and zinc stearates;
(F) Polyoxyethylene, polyoxypropylene block polymers—Pluronics; and
(G) Ethoxylated fatty alcohols.

In large part the selection of a gelling agent is a function of the type of gel desired which relates directly to the intended use of the product. The physical properties which must be exhibited, in combination with the ingredient make-up of the formulation will offer strong indication as to which gelling agents should be selected. Whereas natural gums have proven to be efficient gelling agents in the case of formulations with high concentrations of water, metallic stearates are known for their efficient gelling properties with formulations which contain alcohols and/or glycols. Since evaporation is the operative process in the delivery mechanism of a gel-based air freshener, non-volatile components should be kept to as low a concentration as can be tolerated. The gelling agent therefore should be kept at functional minimums and its non-volatile contribution kept purposefully low.

Gels traditionally used for air freshening systems are mixtures of carrageenan, locust-bean gum and other water-soluble polymers and gums. The gels may readily be prepared by cooling a relatively concentrated dispersion of these gums in hot water. As the solution cools the highly hydrated dispersed particles agglomerate into larger masses and eventually mat together to form a semi-rigid gel structure that entraps any free water. Materials that are effective as gellants produce these large complex moieties which have this capacity to link together in a coherent mesh-like network such that the liquid becomes immobilized, thus forming the gel. Gels of this type are generally considered to belong to an erodible class of air fresheners where volatilization is the mechanism of erosion. A detailed discussion on the use of carrageenan and locust bean gums for the purpose of fabricating air freshener gels can be found in U.S. Pat. No. 4,056,612.

Air treating gels provide an effective means for the gradual introduction into the air of volatilizable air treating components, including for example, air freshening and odor counteractant components. In commercial use of such gels, it has generally been the practice to pre-fashion bodies or slugs of gels having a suitable shape and contour, and then place the preformed bodies in a desired container or dispenser. More recently, in U.S. Pat. No. 2,949,710, a departure from this procedure has been disclosed, in which a cup-shaped top and multi-fingered base dispensing container are liquid filled in an inverted position and returned to the normal upright position during solidification of the gel. In order to provide for separation of the parts to expose the gel for use, the base part carries an internal tapered core extending through the body of gel to a void space at the top of the assemblage from which the body of gel will readily separate as the cup part with the gel body adhering thereto, is lifted from the base. This action permits a flow of air to the void space above the gel body, permitting the gel body to slide by gravity down the elevated cup to rest upon the base and be exposed between the fingers thereof. This approach has certain disadvantages for practical use. For one, the gel will sometimes adhere tightly enough to the cup part, so that the admission of air and the force of gravity, even with shaking, will not readily cause the gel body to separate from the cup. Another disadvantage is that the tapered core on the base displaces a substantial volume of gel in the area of the gel body which is subject to most rapid shrinking through evaporation of the volatile components during use, with the result that the desired uniformity in evaporation rate cannot be achieved.

The foregoing discussion of the prior art was taken in part from U.S. Pat. No. 3,239,145 to A. D. Russo which proposed liquid filling of a dispensing container with an air treating gelling agent wherein means are provided in the base part for establishing an extensive zone of anchorage between the gel body and base part which, coupled with a very slight taper in the wall structure of the cup part, permits the cup part readily to be separated from the gel body by a combined rotary and longitudinal movement when it is desired to open the container and expose the gel for initial air treating use.

Evaporation progressing only when the device is open and being arrested when the device is closed.

Each of the prior art devices has some disadvantages such as high cost, inadequate rate of release of fragrance, difficulty in forming and maintaining a desired shape. The subsequent description will illustrate the highly complex methods used in a commercially available prior art device developed in order to provide a sustained fragrance delivery from a carrageenan based air freshing gel.

More particularly, as shown in FIG. 1 of the drawings the dispenser-container in accordance with U.S. Pat. No. 3,239,145 comprises a base part 10 and top or closure part 11, each comprising a unitary body of molded plastic material such as polyethylene or polypropylene.

The parts are of generally circular cross-sectional form with the base 10 comprising a cup-shaped closed bottom 12, and an intermediate tapered zone 13 which flares slightly in the direction of an upper portion 14 which is of slightly larger diameter than the bottom portion 12, and has a plurality of upwardly extending spring fingers 15, four being shown for purpose of illustration. The spring fingers 15 have elongated inwardly protruding radial ribs 16 which provide both effective stiffening means for the spring fingers, and substantially line contact with outer surfaces of the top or closure part 11.

The closure part 11 is an essentially cylindrical cup having a closed end 17 and slightly tapered side walls 18 extending to an open end 19 of larger diameter than the end 17, having at the outer periphery thereof a tapered or beveled surface 20 adapted to provide sealing engagement with the tapered zone 13 of the base 10.

Closely adjacent the beveled surface 20, the closure member 11 is provided with a plurality of circumferentially spaced protruding lugs 21, having a slightly convergent taper, for interengagement with corresponding circumferentially spaced lugs 22 protruding from inner surfaces of the upper base part. According to the patentee, the number of lugs 21 and 22 should correspond with the number of spring fingers 15, in order that the lugs 21 when disengaged from the lugs 22, can slide vertically between the spring fingers 15 and the protruding ribs 16 thereof. The lugs 21, 22 when brought into engagement by rotary movement of the closure part 11 with respect to the base 10, force the tapered portion 20 of the closure part into close vapor sealing engagement with the tapered zone 13 of the base. In order to prevent too tight a closing action, at least two opposed lugs 21 have at the wider ends thereof, a supplemental protruding lug 23 which acts as stop means, limiting rotation of the parts.

In the use of the device, the top or closure part 11, is oriented with the open end 19 at the top, and is filled with air treating gel in liquid form. While the gel is still in liquid form, the base part 10 is slid over the closure part 11, and the parts are relatively rotated to provide a vapor-tight seal therebetween as above described. The assemblage is then inverted to the upright position shown in FIG. 1, at which point the liquid gel flows into the base 10, establishing a new upper level 25, leaving a substantial void space 26 adjacent the closed end 17 of the closure part. In this position, the gel is allowed to solidify to a gel mass 27.

The bottom wall 28 of the base 10 is provided with an inwardly extending cylindrical member 29, forming a central circular recess 30 in the base 10, which is closed by a supplemental bottom wall 31 traversing the cylindrical member 29, and forming therewith a shallow recess 32 within the base 10.

The cylindrical member 29 and supplemental bottom wall 31 provide a substantial and irregular surface area within the base 10 to become embedded in the solidified gel 27. The anchorage of gel thereby provided purportedly supports the gel mass 27 against rotation with respect to the base as the closure part 11 is rotatably moved to disengage the lugs 21, 22. The closure part can then be raised to the open or operative position so that air may circulate around the exposed gel mass between the spring fingers 15, to permit gradual introduction of volatilizable components from the gel into the surrounding air. The closure part 11 is readily supported in any desired position of elevation by the spring fingers 15, thereby providing substantial variations in the rate at which evaporation of volatilizable components can proceed.

As will be appreciated the dispensing container for air treating gel disclosed in Russo U.S. Pat. No. 3,239,145 requires a number of close tolerance parts which are relatively expensive to produce and assemble, thus negating the otherwise low cost advantage of gels. Moreover, the Russo dispensing container may be susceptible to liquid loss during filling, i.e. prior to complete gelation of the filling, due to incomplete sealing in the filling position.

Other partial disadvantages and problems associated with the use of a gel for sustained fragrance delivery include:
(A) Tendency for syneresis, i.e. the exudation of water from the gel surface which imparts a wet and unpleasant visual appearance;
(B) Typically short functional life;
(C) Poor mechanical strength and shrinkage;
(D) Diminishing size and surface;
(E) Relatively large size;
(F) Realatively heavy weight, i.e. with a unit typically weighing 200 g.–300 g.;
(G) Unsightly appearance of the shrunken, spent gel;
(H) Poor freeze-thaw stability; and
(I) The necessity to provide a secondary means of controlling the rate of release.

The rate of release with regard to gel based air fresheners is initially high which is then followed by a rapid decline. The amount of release of the active agent may initially exceed the amount required for effective air treatment while at some later time it may be inadequate for the task.

It is thus an object of the present invention to provide a novel and improved dispensing device which overcomes the aforesaid and other problems of prior art dispersing devices. A more specific object of the present invention is to provide a novel and improved dispersing device which is characterized by low cost manufacture, ease of filling, and performance efficacy. Still another object of the present invention is to provide a despersing device particularly adapted to use with air freshener gels which capitalizes on inherent advantages of air freshener gels and which minimizes or overcomes prior art disadvantages normally associated with the use of air freshener gels. Yet another object of the present invention is to provide a system for the delivery of air treating agents which avoids an initial high rate of release in favor of a more controlled release of said agents to the atmosphere. Yet other objects and many of the attendent advantages of the present invention over the prior art will become clear from the description which follows.

The invention accordingly comprises the processes involving the several steps and relative order of one or more such steps with respect to each other, and apparatus possessing the features, properties and relations of elements which are exemplified in the following detailed disclosure and the scope of application of which will be indicated in the claims.

Generally, to effect the foregoing and other objects of the present invention provides an air treating device comprising a container for holding an erodible gel, and having an opening covered at least in part by a rate-modifying membrane in intimate contact with said erodible gel. The membrane is a material which is capable of:

(A) accepting the gel in the liquid state either superficially or intimately within its matrix such that a physical attachment may be established between the two; and (B) controlling the rate of evaporation of the gel and the air treating agents contained therein by allowing transmission through its open matrix at a sufficient rate so as to satisfy a desired performance criteria and yet maintain an efficient and sustained rate of delivery.

Completing the air treating device in accordance with the present invention are means for containing the aqueous solution of gelling agent within the container until this liquid gel sets at least in part. Such means may be inherent in the membrane, or may be provided by a separate, liquid impervious member disposed to the outside of said membrane.

The use of membranes for the purpose of releasing air treating agents on a sustained basis have typically functioned by permitting passage of the active agents through a polymeric barrier in the absence of pores or holes by a process of absorption of the active into the barrier layer, followed by its dissolution into the barrier and subsequent diffusion. Typically the diffusivity through this membrane is relatively low, especially when considering the transmission of relatively large molecules through dense polymer membranes. The use of an extender or dilution medium which is capable of solubilizing the active agent but which is also capable of permeating and plasticizing the membrane is a common method for providing rate control in these plastic type membranes. Extenders and diluting vehicles suited for this purpose by necessity are organic in composition due to the plastic nature of the membrane barriers. Water which is the most economic and common of diluents proves particularly unsuited for use with these types of membrane sustained delivery devices.

The ability to take advantage of an aqueous based reservoir and other advantages of the present invention may be seen from the following detailed discussion which should be considered in conjunction with the accompanying drawings wherein:

FIG. 1 is a diagrammatic view of a prior art air treating device made in accordance with the teachings of Russo, U.S. Pat. No. 3,239,145 as discussed previously;

Figure 2:
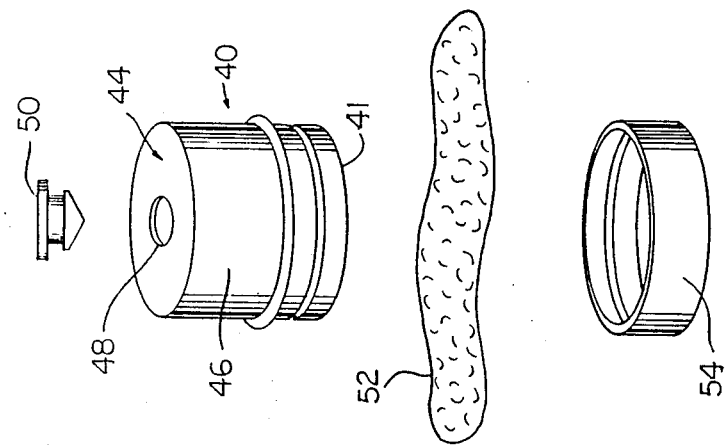
FIG. 2 is a diagrammatic exploded view of an air treating device made in accordance with a preferred embodiment of the present invention.
Figure 1:
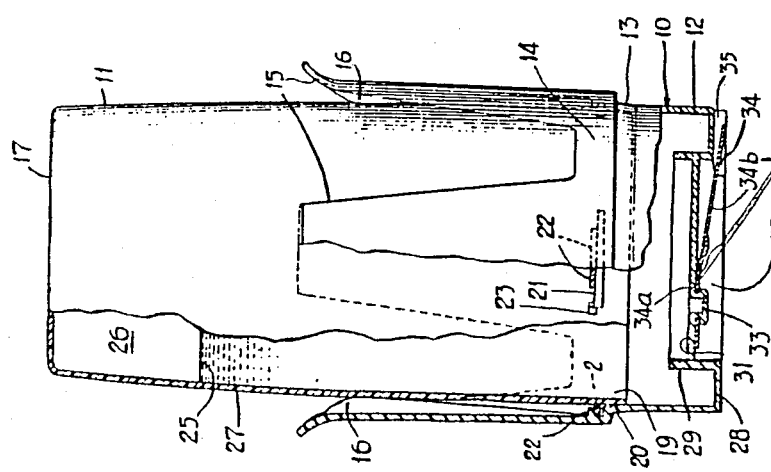
Figure 4:
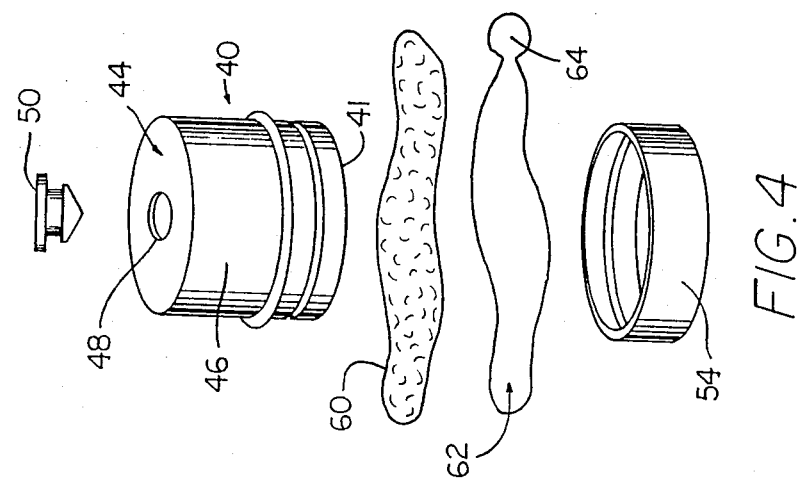
FIG. 4 is a diagrammatic exploded view, similar to FIG. 2, illustrating an alternative form of air treating device made in accordance with the present invention.

For convenience of illustration FIGS. 2, and 4 are shown inverted.

Referring particularly to FIG. 2 of the drawings, the gel container assembly comprises a reservoir type air treating device comprising a container, indicated generally at 40 for holding a supply of an erodible gel. Container 40 is open at one end 41, and may be made in a variety of shapes of conventional design, and typically comprises a flat bottom wall 44, generally circular in plan, and substantially vertical side walls 46. An aperture 48 is formed through bottom wall 44, is sealed by suitable sealing means or plug 50. The purpose of aperture 48 and sealing means or plug 50 will become clear from the description following. Container walls 44 and 46 and closure means 50 should be formed of material which is impervious to the gel and components thereof contained therein whether in liquid, gel or vapor phase. Typically container 40 and closure member 50 will be formed of a synthetic polymeric material such as polyethylene, polypropylene or the like which may be formed in desired shape by molding. Closure member 50 may comprise a snap or screw fitted plug. Alternatively, closure member 50 may comprise a sheet member or tape formed of a material which is impervious to the gel and components thereof, fixed to the bottom surface of bottom wall 44 by suitable means such as an adhesive.

Container 40 open end 41 is covered by a membrane indicated generally at 52 as will be described in detail hereinafter. Membrane 52 is fixed over the top of container 40 by suitable means. For ease of manufacture membrane 52 may be made slightly oversized so that it may be captured between and held in place by a press fitted ring 54 which is placed over the membrane 52 and onto the container side walls 46.

An important and critical feature of the present invention resides in the selection of the membrane material. The membrane material should be one which is sufficiently permeable to the aqueous solution of the liquid gel so as to permit penetration of this liquid gel solution sufficient to physically attach to the membrane once the liquid has solidified so that the membrane can support the entire weight of the solidified or cast gel once the container is turned upright. The membrane material also should be capable of controlling the rate of evaporation of the gel and the air treating agents contained therein by allowing transmission through its open matrix at a sufficient rate so as to satisfy a desired performance criteria and yet maintain an efficient and sustained rate of delivery. Preferably, but not necessarily, the membrane material will be wetted only in a limited fashion by the heated liquefied gel solution, for reasons that will become clear from the description following.

In the manufacture of an air treating device in accordance with the present invention, the container is assembled with all elements in place except for the closure member 50. The air treating device is then inverted, i.e. so that the membrane-covered open end is oriented downward, and the heated liquid gel solution containing the desired air treating agents, is loaded into the inverted container through aperture 48. As noted supra, membrane 52 should be formed of material which is sufficiently permeable to the aqueous solution of liquid gelling agent so as to permit permeation into the membrane at least in part. However, the liquid gel should be retained in the container with little or no liquid passing completely through membrane 52 by suitable retaining means as will be described in detail hereinafter. The container may then be closed on its bottom by means of closure means 50, and the gel permitted to set. The set gel, being at least partially permeated into the membrane, attaches to the membrane. Once the gel is fully set, the container may then be oriented, i.e. where it is ready for use. In order to avoid loss of contents on the shelf, the container may be sealed within suitable, i.e. vapor impervious packaging means (not shown) in known manner.

As noted supra, the novel air treating device in accordance with the present invention permits the dispensing of fragrance from a gel based reservoir through a porous permeable membrane which intimately contacts the gel at the interface of its evaporative surface and the surrounding atmosphere. The membrane should be capable of accepting the gel in the liquid state so as to serve as a point of attachment to the gel. On the other hand, the membrane should be capable of controlling the rate of evaporation of the gel and air treating agents contained therein, and in a preferred embodiment of the invention, of sealing against the passage of the liquefied gel solution so that the liquefied gel solution can be loaded onto said membrane from an opening on the reverse side of said container. In such embodiment the membrane must be capable of supporting the full load of the gel solution, which constitutes the fragrance reservoir, without allowing the passage or leakage of any substantial portion of the gel solution therethrough during the gel solution filling process. Moreover, the membrane should not be occlusive, since a porous nature is necessary in order to permit the evaporation of the contents of the reservoir. The membrane also must be of a composition which is not so repulsive to the liquid reservoir formulation that intimate contact is prevented from occurring between the substrate and reservoir, i.e. such that a physical or mechanical attachment cannot be established between the two.

Thus, the selection of an appropriate material for use as membrane 52 in the type of device disclosed herein is dependent not only upon the ability of that membrane material to influence the rate of evaporation with respect to the gel and air treating agents contained therein, but also, in a preferred embodiment of the invention, its ability to exhibit desired controlled or delayed penetration characteristics with respect to the hot filling of the liquid reservoir. Thus, in a preferred embodiment of the inventions, the porous membrane material should be one capable of delaying complete penetration of the liquid gel solution through the porous membrane for a sufficient length of time to permit the gel to set, at least in part. The ability of the membrane to accept the liquefied gel solution but not to permit its passage through this substrate establishes one criteria for performance of preferred membrane materials. The physical attachment between the gel, once it has set, and the membrane should be of sufficient strength so as to keep the gel intimately in contact with the membrane independent of the positional orientation of the device for a period that extends for the evaporative life of the reservoir, i.e. it should be of sufficient strength to support the entire weight of the cast gel. In this way a continuously fresh gel surface will continually feed into the emanating surface of the device such that odor awareness will remain substantially uniform. The dispensing rate of the device also will be dependent on the surface area, the membrane composition, thickness and porosity. One skilled in the art would thus select a membrane having the most desired effects upon the dispersing rate for the selected reservoir formulation. The air freshener of the present invention can be easily manufactured and can include sufficent fragrance for as little as one week effective time or up to six weeks effective time. The effective life of the unit is principally a function of the size and type of emanating surface selected as well as the size of the reservoir and the concentration of active material dispersed therein.

As mentioned previously, the preferred membrane for use in the device described herein should be selected from materials having the following physical characteristics:

(A) capable of containing a liquid gel solution within the container until gellation is established at least in part;

(B) capable of accepting the gel solution either superficially or intimately within its matrix such that a physical attachment is established between the two; and (C) capable of controlling the evaporation of the reservoir and the air treating agents contained therein by allowing transmission through its open matrix at a desired rate.

Typically, the liquid gel reservoir comprises a heated aqueous based solution, and gellation occurs by cooling the heated solution.

Amongst materials as may meet the aforesaid criteria and thus be suitable as preferred membrane materials for use in accordance with the present invention are mentioned:

(A) Polydimethylsiloxane-treated porous substrates such as cellulosis, synthetic textiles, foams, and porous plastics treated with a suitable material such as this silicone polymer to provide an intimate coating of these substrates;

(B) Adhesively bound non-woven substrates such as non-woven synthetic textiles which utilize binders which impart a hydrophobic water resisting character to the textile;

(C) Woven and non-woven and felted fabrics such as natural and synthetic textiles of sufficient weight (2 oz./yd.$^2$ or greater) which, due to their mass and fiber density per unit area, require a longer penetration time. This permits sufficient time to transpire so as to allow the gel solution to set before complete penetration and leakage through the textile can result;

(D) Porous Plastics that are porous in nature and are characterized by a pore size and void volume selected to provide the aforesaid desired physical characteristics for the particular gel being utilized, such as porous polyethylene and porous polypropylene; and (E) Foamed Polymeric materials that are porous, absorbent and characterized by a void volume and pore size to provide the aforesaid desired physical characteristics for the particular gel being utilized, such as polyether, polyester, polyurethane and polyvinylalcohol formal foams.

The suitability of a membrane material to perform in the manner desired is dependent on the gel compositions used as the fragrance reservoir. Thus, in selecting a suitable membrane material one first must select the gel composition. Consider, for example, carrageenan based aqueous gels which represent the commercially preferred formulations for air freshening gel reservoirs. Typically carrageenan based gels contain relatively high concentrations of water (e.g. 70%) and as a result possess high surface tensions even at elevated temperatures in the solution state. On the other hand, metallic stearate-based gels, which have also been used commercially as a fragrance reservoir for gel air fresheners which contain, for example, 42% water and 30% ethanol, exhibit significantly reduced surface tensions in the hot solution state due to the concentration of the alcohol present, and this contributes to a solution with greater penetrating capacity. A membrane particularly suitable for use with both carrageenan based gel formulations and water-alcohol gel formulas comprise a porous flexible textile substrate, such as a porous cellulosic substrate material in which the individual fibers are coated with a silicone polymer material. Such a membrane material may be prepared from a lightweight (2.5 oz./yd.$^2$) cellulosic substrate material by impregnating the substrate using a wet coating process, with a reactive, curable polydimethylsiloxane polymer. The polymer intimately coats the fibers of the substrate material and imparts a durable water-repellant hydrophobic character thereto.

The amount of silicone deposited onto the substrate material should be sufficient to provide a substantially uniform coating of all the fibers, but not in such quantity as to completely occlude the natural voids and passages of the substrate material. A cellulosic substrate material may be any fibrous, woven or non-woven substrate formed from a cellulosic material such as cotton, paper, cardboard, pulp and the like.

The curable polydimethylsiloxane produces an intimate coating of the fibers which make up this lightweight cellulosic substrate and yet does not completely occlude the porous matrix nature of the substrate. However, the coating does occlude the porous nature of the substrate somewhat depending on the amount of polydimethylsiloxane deposited onto the fabric; i.e. as the amount of polydimethylsilioxane is increased, the pore size and open nature of the substrate is correspondingly reduced.

Preferably the non-woven fabric selected for use as the substrate upon which to deposit the silicone in preparation of the membrane consists of two layers of cellulose tissue heat set to a scrim-reinforced web such that no adhesive binder is utilized in the construction. The fabric weight is 2.5 oz./yd.$^2$ and is sold commercially by the Kimberly-Clark Corporation under the tradename Kaycel 6910. Fabric weights on the order of from 1 oz./yd.$^2$ to 4 oz./yd.$^2$ are suitable for this application depending upon the type of properties required of the membrane and the desired release rate required per unit area.

Heavier fabric weights, due to increased fiber density and thickness, will exhibit a reduced porosity versus those substrates of lighter construction. However, the heavier weight fabrics used need not necessarily be loaded with higher amounts of the polydimethylsiloxane polymer, since the solids concentration of the processing solution can be adjusted to compensate for such tendencies.

The silicones selected for use as the coating agents are commercially available in a variety of compositions from a variety of manufacturers. Presently preferred silicones are the Silicone Paper Release Additives and Silicone Paper Release Catalyst which are available from the General Electric Company's Silicone Products Division. These are materials comprising reactive polydimethylsiloxanes of sufficiently high molecular weights so as to be considered "silicone polymers".

When the degree of crosslinking is low, an elastic material, silicone rubber, is produced. This composition can be represented by the formula:

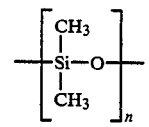

which reflects the dimethylsiloxane crosslinked through the Si—O bonds which ultimately finds application as the polymeric coating for the textile substrate.

The silicone solutions may be applied to a substrate material using a variety of methods, including: spraying, brushing, dip-coating, and roll-coating. The traditional useage for these silicone solutions has been for the preparation of non-stick release coatings for use on paper, foil and plastic substrates as well as in providing water repellancy for textiles and leathers. The commercial designation used for these compounded reactive silicone fluids as provided by the General Electric Company in their technical product bulletins is provided in Table 1. Reference is also made in this table as to whether the crosslinking agent Polymethyl Hydrogen Siloxane (SS-4300C) need be incorporated with the silicone solution in order to initiate polymerization. Recommended use levels for the crosslinking agent and cure temperatures are all provided in the appropriate technical product data available from the General Electric Corporation.

TABLE I

| GENERAL ELECTRIC Trade Name | Silicone Content % | Chemical Name | Chemical Family | Crosslinking Agent Required |
|---|---|---|---|---|
| SS-4300 | 100 | Polymethylvinylsiloxane Copolymer | Polysiloxane | Yes |
| SS-4330 | 30 | Polymethylvinylsiloxane Copolymer | Polysiloxane | Yes |
| SS-4335 | 35 | Siloxane Resin | Silicone Resin | Yes |
| SS-4400 | 100 | Methylvinylsiloxane | Silicone Fluid | Yes |
| SS-4273 | 100 | Polydimethyl Siloxane Resin | Polysiloxane | No |
| SS-4098 | 50 | Dimethyl Polysiloxane Resin Solution | Polysiloxane | No |
| SM-2138 | 60 | Dimethyl Silicone Fluid Emulsion, Aqueous | Polysiloxane | No |
| SF-99 | 100 | Methyl Silicone Fluid | Polysiloxane | No |

All of the silicone fluids listed in Table 1 will form an intimate and durable coating on cellulosic type substrates. (Similar compounded reactive polydimethylsiloxane solutions are available under the trade name Syl-off from the Dow Corning Corporation.) Silicone loadings may be varied depending on the degree of occlusion which is required in order to achieve the desired effect upon the permeability of the membrane.

MEMBRANE PREPARATION

A standard procedure for the preparation of a membrane utilizing a textile substrate and a reactive silicone fluid requiring the use of a crosslinking agent and thermal cure is as follows:

A bath of the reactive silicone, crosslinking agent, and volatile solvents is prepared according to the following formulation:

| | |
|---|---|
| Toluene | 20.0 parts |
| Hexane | 4.0 parts |
| SS-4330 | 14.0 parts |
| SS-4335 | 6.0 parts |
| SS-4300C | 0.2 parts |

A preweighed and premeasured strip of non-woven cellulosic fabric was then immersed in the bath and the excess solution squeegeed off. The treated fabric was then placed in a 70° C. convection oven for 10 minutes to effect the thermal cure of the polymer. After this time the sample was allowed to equilibrate to ambient temperature and was then reweighed so that a loading could be determined. The term "loading" will be used to refer to the amount of polydimethylsiloxane which remains on the substrate after completion of the processing with the silicone solution and subsequent drying. The loading is calculated in mg./in$^2$ by using the following formula.

Loading =

$$\left[ \frac{\text{wt. treated substrate(g)} - \text{wt. untreated substrate(g)}}{\text{Area of Substrate (in}^2)} \right] \times 1000$$

An indication of the degree to which the character and properties of the non-woven substrate change as a function of the silicone coating is illustrated through the use of a Vertical Wicking Height Test comparing treated and untreated fabrics. The treated fabric used in this test was prepared in accordance with the aforementioned procedure. The fabric used was the Kaycel 6910 2.5 oz./yd.$^2$ material and the resulting loading, based on the use of the bath formulation just cited, was 10.8 mg./in$^2$.

VERTICAL WICKING HEIGHT AND INITIAL WICKING HEIGHT

This test with minor modifications was adapted from the publication entitled "Liquid Wicking Rate: Capillary Test of Paper", TAPPI Useful Methods, 451. It is referred to in the claims as the "Standard Wicking Test".

Samples cut for this test were rectangles 13 cm. in the machine direction and 2.54 cm. in the cross machine direction. The sample was clamped at one of its shorter sides so that it hangs with the machine direction of the fabric essentially vertical. A millimeter scale was clamped adjacent and parallel to the sample but not in contact with it. A reservoir of the liquid material then was brought in contact with sample so that the liquid level corresponded to the zero mark on the millimeter scale and the lower extremity of the sample was just below the surface of the reservoir.

The height of liquid in the wick was measured by comparing the height of the advancing head of liquid in the sample to the millimeter scale. Initial wicking height was the height attained by the liquid after three (3) minutes have elapsed; total wicking height was defined herein as the height attained by the advancing head of liquid after one (1) hour has elapsed. The results of this test run with a variety of solvents in the reservoir are shown in Table 2.

TABLE II

| | WICKING TEST RESULTS | | | |
|---|---|---|---|---|
| | Time: 3 Minutes | | Time: 1 Hour | |
| RESERVOIR FLUID | TREATED | UNTREATED | TREATED | UNTREATED |
| WATER | 0 mm | 40 mm | 0 mm | 96 mm |
| DIPROPYLENE GLYCLOL MONOMETHYL ETHER | 8 mm | 26 mm | 20 mm | 64 mm |
| PROPYLENE GLYCOL | 0 mm | 19 mm | 4 mm | 53 mm |
| HEXYLENE GLYCOL | 5 mm | 17 mm | 10 mm | 46 mm |
| SD ALCOHOL 40 (190 Proof) | 15 mm | 20 mm | 15 mm | 26 mm |
| WATER/SD ALCOHOL 40 (1:1) | 0 mm | 24 mm | 5 mm | 72 mm |

The difference in characteristics between the silicone-treated substrate and that which is untreated is seen by comparison of the water wicking height results. When water was used as the liquid in the reservoir, the treated substrate showed no wicking even after one hour, whereas in the case of the untreated substrate and water we observe the highest recorded values for this test at both the three minute and one hour intervals (40 mm. and 96 mm. respectively). In the case of the 1:1 mixture of water and alcohol we see that with treated fabric the addition of water to an otherwise rapidly wicking liquid (alcohol) can cause a significant reduction in the wicking height as compared to those values recorded for that substance when no water was present. At the one hour interval with the treated fabric the 1:1 mixture of water and alcohol rose 5 mm. whereas during the same interval alcohol alone registered 15 mm. Conversely with the untreated fabric the addition of water promoted wicking with the one hour evaluation showing a wicking height of 26 mm. for the alcohol alone while the 1:1 mixture registered at 72 mm. The ability of the silicone-treated membrane to resist wetting by solutions which possess an aqueous character imparts to this membrane those characteristics which make it especially well-suited for use in the present invention. This is due to the fact that the membrane is resistant to the complete penetration and strike-through which could occur when the aqueous based air freshening gel, which constitutes the reservoir of the air treating device made in accordance with a preferred embodiment of the present invention, is formed by casting the heated liquefied gel directly onto the membrane. Moreover, the failure of the gel to become intimately immeshed in the textile fibers of the membrane allows the membrane to serve as a rate-modifying medium at the interface between the gel and the surrounding atmosphere.

Due to the matrix-like surface of any textile fiber, be it woven or non-woven, when the air freshening gel is cast in its heated liquefied form onto the silicone-treated textile membrane there is a certain physical interaction established between the textile fibers and the liquid. Thus, the air freshening gel solidifying while in contact with the textile fibers establishes a physical contact. This physical contact should be of sufficient strength so as to support the entire weight of the gel and thus permit the operation of the unit in any position, where, for example, the membrane is facing upward and the gel hangs, suspended but intimately attached to the membrane. (The unit of course also is operable from a position wherein the membrane faces downward with the gel on top of it. Operation of the unit in this position assumes the unit is elevated or configured in such manner so as to permit free air flow across the membrane surface.) Weight loss evaluations indicate essentially no difference in performance as a function of position. Due to useage of an erodible gel type fragrance reservoir, there is a significant amount of shrinkage associated with these types of formulations. The shrinkage as evidenced in the commercial gel products of the prior art, results in a diminishing in size of both the height and diameter dimensions of the gel. In the unit disclosed herein, however, the contact adhesion between the membrane and gel surface and the resulting strength at this interface resists the tendency of the gel to shrink dimensionally in the diameter direction. Thus, the gel reservoir in accordance with the present invention maintains a greater dimensional stability across the full expense of the membrane for the duration of the product's functional life whereby to provide an effective and more uniform fragrance delivery.

The present invention will be more fully described by the following examples wherein all parts and percentages are by weight and all temperatures are degrees Celsius. These examples shall in no way be construed as limiting the scope of the subject of the present invention.

A typical fabrication procedure for an air freshening device based on the use of an evaporation rate-controlling membrane and utilizing a fragrance reservoir consisting of a gel-based fragrance reservoir in accordance with a preferred embodiment of the present invention is detailed below.

A disc-shaped piece of a treated membrane 52 as is cut to sufficient size so as to cover and extend slightly past the edges of an open end 41 of container 40. Container 40 is formed of a liquid and vapor impervious plastic material such as polypropylene. The membrane is then placed over the opening of the container. A locking ring 54, preferably of plastic material, whose inside diameter is just slightly larger than the outside diameter of the container opening has a continuous ridge (not shown), which runs completely around its inside surface. This locking ring is then pressed over the membrane onto the neck of the hollow container 40. The neck of container 40 has a continuous groove (not shown) running around its circumference on its outside surface such that the ridge 54 of the locking ring comes to rest in this recess on the container neck. The action of sliding the locking ring over the flexible membrane onto the neck of the container and the interference this represents causes the membrane to become stretched over the opening of the container and to become firmly locked in place. The container is then inverted, and the inverted container is loaded by pouring liquefied air freshener gel through the fill hole aperture 48 located in the bottom wall 44 of the container. When fully loaded, the aperture 48 is sealed with a resilient compressible expansion plug 50, and the loaded container is kept stationary until the gel cools and becomes firm.

EXAMPLE I

Preparation A

Dispersing Unit Preparation

A disc-shaped membrane was cut from a sheet of silicone treated non-woven cellulosic fabric, Kaycel 6910, which was coated with a curable polydimethylsiloxane in sufficient quantity so as to achieve a loading of 10 mg./in$^2$ utilizing the silicone coating formulation previously referred to under "membrane preparation", and assembled into a dispersing unit as described below.

The dispensing unit consisted of a hollow 2-ounce plastic container 40 with cylindrical walls 46 and a 2-inch diameter opening at one end while at the substantially closed end 44 there was a 0.5-inch diameter fill hole 48. The full surface area encompassed by the major opening of the container was 3.14 square inches. The silicone treated membrane 52 was next positioned over this opening and tautly secured in place over the mouth of the container as a locking ring 54 was pressed over the fabric onto the neck of the container.

Preparation B

Gel Preparation

The following ingredients are assembled:

| Ingredients | Weight Percent |
| --- | --- |
| Water | 74.90 |
| Propylene Glycol | 13.50 |
| Dipropylene Glycol Momomethyl Ether | 5.00 |
| Colloid 878* TIC GUMS, INC. | 1.90 |
| Sodium Stearate | 1.50 |
| Fragrance | 3.20 |
| Preservative, Color | q.s. |
| | 100.00 |

*Colloid 878 is a blended mix of Carrageenan gum, salt and guar gum.

The gel is prepared by dispersing the Colloid 878 together with the other ingredients in the water, and the resulting solution heated to 180° F. to effect solution. The more volatile components, including the glycol ether and fragrance, are added just prior to the completion of the solution step to minimize their evaporation due to the high processing temperatures. The resulting solution is then cooled to room temperature to provide the finished air freshener gel.

The fragrance used in this air freshener may be any conventional and commercially available fragrance as typified by florals, citrus, mints, fruits, pine, spice, herbal and other various formulated bases. The precondition to the use of a fragrance oil is that they do not react with the gel materials and that it is heat stable at the temperatures employed in the formation of the gel. The fragrance may comprise one perfume but typically this represents a blend of from about 15 to about 150 different fragrance aroma chemicals. The fragrance level is readily adjustable. A fragrance level concentration of 3.20% by weight was selected for use in this invention since a more concentrated formula permits the fabrication of dimensionally smaller units while still maintaining approximately the same amount of fragrance utilized in a larger unit. The concentration of active ingredient may be selected by the practitioner in accordance with their own particular needs with regard to intensity and duration of fragrance and the like.

The unit was next loaded by filling the container with 60 grams of the freshly prepared gel. The filling operation is carried out while the gel is still liquid, at a temperature of 70° C.; the gel is poured through the fill hole onto the membrane. Once completed the fill hole is closed by means of a compressible plug. In this example a fresh floral fragrance was selected as the perfume for demonstration. The container after filling is kept stationary until the gel solidifies. The unit is then wrapped with foil and allowed to fully equilibrate to ambient temperature. The addition of the freshly prepared gel onto the membrane may result in the passage of some vapor through the membrane at an accelerated rate. No penetration or leakage through the membrane by the gel solution was evident, and the excess vaporization through the membrane subsides as the gel solidifies. The loss due to the hot vapor permeation through the membrane accounted for a loss of about 1.5% of the fill amount.

The units fabricated in this manner are then evaluated for their sustained odor production through an evaluation whereby the unit is placed in a closed room 900 cu. ft. in volume while a commercially available small space blotter type air freshening unit is placed in a room of identical configuration. The products evaluated contained similar amounts of fragrance. The purpose of using a commercial unit is to provide an odor intensity standard so that the evaluation will yield results indicating commercial potential. A specially trained panel is then permitted to enter both rooms 1 hour after the introduction of the air freshening unit into each room. The panel is then asked to record their response with regard to their prceived motion as to odor intensity using a standard scale. This comparative evaluation is conducted every fifth day for a period of 30 days. The results from this evaluation indicates that the disclosed membrane-gel type unit is a more effective device for creating odor awareness and performs in a more uniform way than was evident in the commercial blotter type control. Weight loss evaluations conducted during this 4-week period show that the membrane-gel unit loses 80% of its reservoir weight during this period indicating the pervious nature of the membrane and the substantial release potential of a unit of this size and configuration.

Another method of evaluating the influence of a porous permeable membrane in intimate contact with the emanating surface of the gel reservoir, in addition to odor evaluation tests, is to measure the membrane's effect upon the weight loss characteristics of that unit. Losses measured during this period are a function of the evaporation of the volatile components of the gel formulation which includes water, co-solvents and fragrance. The goal of producing an extended functional life usually through fragrance fixation or through package design engineering has been the subject of considerable effort in the prior art. Influence over the inherent evaporative nature of the volatile reservoir formulation is routinely sought so as to prolong the perception of effectiveness while minimizing the reservoir size for purposes of economy. Typically, units must be sized in such a way so as to deliver an adequate dosage of fragrance particularly in the latter stages of the products functional life so as to meet the commercial expectations of the consumer. Consequently, large diffusion surfaces, which produce inordinately high losses in the first few days of the operational life of the unit are so required as to provide a sufficient release rate as the product matures and becomes spent. Saturated blotter type substrates are especially susceptible to this type of uncontrolled loss whereas gels have traditionally offered a more uniform release. However, if the use of a porous permeable membrane of the configuration described herein can be shown to demonstrate an ability to exert some regulatory influence over the release characteristics of the gel composition, then the potential for fabricating effectively performing units of reduced size presents itself. The option of using a larger emanating surface so as to maximize the potential for its interaction with the surrounding atmosphere also becomes a possibility if the expanded surface can be controlled and does not necessitate the use of a larger reservoir. The utilization of this membrane technology and the optionstha it creates can be considered an enhancement to the under-utilized gel delivery mechanism. The abiliity of the membrane to enable the fabrication of small, concentrated, efficiently performing sustained delivery devices creates the opportunity for the dispensing of agents in addition to fragrance which up to this time might have been regarded as unsuited to this method of delivery.

A series of air freshening units were prepared utilizing the same basic construction as in Example I with the exception that a variety of different membranes were used in this comparative test. These units were compared in their weight loss characteristics to a similarly constructed and formulated control sample which used no membrane and presented a clear and unobstructed gel surface at its major opening. The construction of these units consisted of a 2 ounce container as exemplified by the design in FIG. 2 which has a 2 in. diameter opening over which was fixed a selected membrane. A fresh, floral fragrance, de Laire Bouquet DL 21801, was used at a concentration of 3.2% in the gel composition described in Preparation B-Gel Preparation. A fill of 58 grams was loaded into the container by means of the fill hole on the reverse side and a period of 24 hours was allowed to pass to allow the units to stabilize before conducting the weight loss evaluations.

The membranes selected for use in these test units were chosen experimentally based on their suitability to contain the gel formulation during the hot fill process as well as for their favorable influence in providing for a regulated rate of release. The series presented accounts for membranes of the following composition and construction:

polysiloxane treated non-woven fabrics, Units 2 and 3
rigid porous plastic compositons, Units 4 and 5
foamed polymer, Unit 6 a non-woven fabricated with an adhesive binder which imparts a limited controlled aqueous penetration, Unit 7.

Gravimetric weight loss evaluations were conducted at 10 day intervals over a 30 day period. The temperature variation over the course of the test was small, with a median temperature on the order of 24° C.

Table III details the component characteristics of the selected membranes and the weight loss values for the units prepared with those membranes. These values are recorded along with the weight loss data for that of the control unit. The weight loss information displayed in this table accounts for losses registered during each of the 3, 10 day intervals, along with a value for the total recorded loss for the entire 30 day period.

A comparative evaluation of the magnitude of the difference in the weight loss characteristics of the membrane-gel test units versus that of the control was tabulated in Table IV based on the use of the following equation.

% Difference from the Control =

$$\frac{\left[\dfrac{10 \text{ day wt. loss}}{\text{Exptl. Unit}} - \dfrac{10 \text{ day wt. loss}}{\text{Control Unit}}\right]}{[10 \text{ day wt. loss for Control Unit}]} \times 100$$

It is the purpose of this table to provide a readily apparent comparison of the evaporative profile of the test units during the initial, middle and latter stages of the product's intended functional life as compared to that of the control. As is evident from this calculation the reporting of a negative percent difference, indicated the presence of a retarding influence on the part of the membrane as compared to the control whereas a positive percent difference illustrates a release rate in excess of that which was recorded for the control unit.

TABLE III

| | Unit 1 [Control] | Unit 2 | Unit 3 | Unit 4 | Unit 5 | Unit 6 | Unit 7 |
|---|---|---|---|---|---|---|---|
| Membrane Type | — | Silicone Treated Non-Woven | Silicone Treated Non-Woven | Porous Polyethylene | Porous Polypropylene | Polyvinyl Alcohol Formal Form | Non-Woven Fabric |
| Supplier | — | Silicone- General Electric Co. Non-Woven Kimberly- Clark | Silicone- Dow Corning Corp. Non-Woven Kimberly- Clark | Porex Technologies Corp. | Porex Technologies Corp. | Shima American Corp. | Contil # 1222128 International Paper Corp. |
| Membrane Thickness | — | .017 in. | .017 in. | .035 in. | .0625 in. | .040 in. | .015 in. |
| Average Pore Diameter | — | Undetermined | Undetermined | 40 micron | 70 micron | 60 micron | Undetermined |
| Silicone Load | — | 8.6 mg./in.2 | 5.5 mg./in.2 | None | None | None | None |
| Interval I Grams Lost Day 1–10 | 32.3 | 24.3 | 26.0 | 21.4 | 24.1 | 29.6 | 26.4 |
| Interval II Grams Lost Day 11–20 | 10.1 | 13.1 | 12.5 | 13.0 | 12.8 | 14.4 | 12.7 |
| Interval III Grams Lost Day 21–30 | 2.3 | 5.4 | 4.5 | 7.5 | 5.1 | 3.1 | 4.6 |
| Total Weight Loss | 44.7 | 42.8 | 43.0 | 41.9 | 42.0 | 47.1 | 43.7 |

TABLE IV

| | | % Difference Versus Control | | |
|---|---|---|---|---|
| | MEMBRANE TYPE | INTERVAL I Day 1-10 | INTERVAL II Day 11-20 | INTERVAL III Day 21-30 |
| Unit 1 Control | none used | 0 | 0 | 0 |
| Unit 2 | Silicone Treated Non-Woven | −24.8 | +29.7 | +139.8 |
| Unit 3 | Silicone Treated Non-Woven | −19.5 | +23.8 | +95.7 |
| Unit 4 | Porous Polyethylene | −33.7 | +28.7 | +226.1 |
| Unit 5 | Porous Polypropylene | −25.4 | +28.7 | +121.7 |
| Unit 6 | (Polyvinyl Alcohol Formal) Foam | −8.4 | +42.6 | +34.8 |
| Unit 7 | Non-Woven with a Water Retarding Adhesive Binder | −18.2 | 25.7 | +100.0 |

It becomes readily apparent from the data as reported in Table III and its treatment in Table IV, that the use of a process which employs a macroporous membrane composition which intimately contacts the releasing surface of an erodible gel reservoir is ideally suited for applications involving the sustained dispensing of volatile air treating agents. This is evident by noting the retarding influence (negative percentages) during the first 10 day interval exerted by each of the membranes of the test units as compared to the uncontrolled loss recoreded for the control. This is typically the effect desired if the enhancement of the gel medium as a sustained release technology is to be effected. Managing the excessive evaporative tendencies of the gel during the early stages of the products functional life so that the reservoir does not become depleted and spent such that it proves insufficient for later duty is the primary principle served by the technology disclosed herein.

Intervals II and III illustrated in Table IV also indicate the type of effect desired in a device designed for this intended purpose.

Namely, the continued release of the air treating agents at a rate which is in excess of that recorded for the control. This has been accomplished due to the deferring of some of the evaporative capacity of the reservoir from the initial interval such that it becomes available for dispensing during these latter stages as represented by intervals II and III. The magnitude of the difference (Table IV) between the control sample and the membrane-gel units is greatest during the final 10 days of the evaluation. This is not unexpected since the control becomes essentially depleted after 20 days. The membrane-gel units on the other hand, due to the fact that they have maintained a greater reserve of gel in the reservoir, are able to register significantly larger weight losses during this final interval. This accounts for the sizeable percentage differential recorded between these units. It is also evident that the membrane composition which is best able to retard evaporation during the initial 10 day interval (Unit 4), due to this reservoir conservation, is in a position to provide the largest release of volatile agents during interval III. This serves to reinforce our principle that deferred evaporative potential can be effectively conserved for later release so as to provide a more uniform and efficient delivery mechanism than can be achieved by a gel which does not benefit from an intimate contact with a macroporous permeable membrane.

The selection of a suitable membrane as previously stated is based upon a number of factors which include:
(A) an ability to contain the gel during the hot fill process due to either a mechanical, physical or chemical induced barrier;
(B) an ability to form a physical attachment with the gel such that the membrane and gel remain affixed to each other for the projected life of the unit; and
(C) an ability to exert an influence over the evaporative nature of the gel.

Certain membranes which may demonstrate good physical attachment may offer little influence over the evaporative rate of the gel. Conversely, membranes which may exert a desired retarding effect upon the evaporation rate may not demonstrate adequate physical attachment to the gel. Thus, the choice of membrane used in the device is dependent of the choice of gel utilized as the reservoir.

Typically gel compositions which contain high concentrations of water, for example, carragaeenan based aqueous gels comprising greaer than about 80 vol. % water possess high surface tensions and as a result, membrane compositionsand structures suitable for use therewith will be different than those useful with reservoir compositions which use different gelling agents containing less amounts of water, e.g. less than about 80%, and volatile co-solvents such as alcohol, for example, ethanol, which exhibit less surface tension and have a greater penetrating capacity and a larger evaporative characteristic associated with them.

As evidence of the ability of a macroporous, permeable membrane of the type described herein to influence the rate of release of a more evaporative reservoir formulation, a metallic stearate gel containing 30% ethanol was prepared. This formulation was used in the fabrication of a membrane-gel type unit along with a control following the same methodology employed in the preparation of the previously cited test units, except that a pour temperature of 45° C. was used along with a 52 gram fill for this formulation. Metallic Stearate Gel Formulation:

| Ingredient | Weight Percent |
|---|---|
| Propylene Glycol | 20.0 |
| Ethanol | 30.0 |
| Water | 42.0 |
| Sodium Stearate | 5.0 |
| Fragrance | 3.0 |
| Total | 100.0 |

The membrane selected was the polysiloxane treated non-woven fabric as previously described. However, the silicone loading applied to this substrate from the formulation listed below was increased over previously cited levels so that a more occlusive coating resulted on the fibers. This was necessary in order to compensate for the greater penetrating capacity of the formulation and its higher rate of evaporation. A silicone loading of 20.5 mg/in$^2$ was applied to the Kaycel 6910 non-woven substrate.

The polysiloxane coating solution used to treat the non-woven substrate for the preparation of the test unit was as follows:

| Polysiloxane Coating Formulation: | |
|---|---|
| Toluene | 9.00 parts |
| Hexane | 10.00 parts |
| SS-4300 | 12.00 parts |
| SS-4300C | 0.12 parts |

A control was prepared using this new gel formulation and weight loss values recorded for these two units over the 30 day test period appear in Table V. The percent difference versus the control as calculated from the interval weight loss data appears in Table VI.

TABLE V

| | Unit 8 [Control] | Unit 9 |
|---|---|---|
| Membrane Type | none | Silicone Treated Non-Woven- |
| Supplier | — | Silicone- General Electric Co. Non-Woven Kimberly-Clark |
| Membrane Thickness | — | .017 in |
| Silicone Load | — | 20.5 mg./in.2 |
| Interval I Grams Lost Day 1-10 | 33.3 | 20.9 |
| Interval II Grams Lost Day 11-20 | 4.8 | 11.7 |
| Interval III | 0.6 | 4.4 |

TABLE V-continued

|  | Unit 8 [Control] | Unit 9 |
|---|---|---|
| Grams Lost Day 21-30 |  |  |
| TOTAL WEIGHT LOSS | 38.7 | 37.0 |

TABLE VI

|  |  | % Difference Versus Control | | |
|---|---|---|---|---|
| | Membrane Type | Interval I Day 1-10 | Interval II Day 11-20 | Interval III Day 21-30 |
| Unit 8 Control | None | — | — | — |
| Unit 9 | Silicone Treated Non-Woven | −37.2% | +143.7% | +633.3% |

It can be seen if these results are compared to those cited previously, that the metallic stearate based gel containing alcohol is a more volatile system. The control loses 86% of its entire evaporative weight during the first ten days compared to a loss of 72% for that of the aqueous based carragaeenan gel for the same period. Due to the larger evaporative rate exhibited by this formula the performance of a rate modifying membrane becomes more accentuated than was evident with the aqueous based reservoir formulation which exhibited a slower evaporative rate.

The ability of the membrane to serve as a rate modifier which reslts in the conserving of some of the evaporative potential of the reservoir is especially evident in this example. The deferred evaporation from the firt interval results in a registered weight loss for the second and third, 10 day intervals, on an order of magnitude significantly in excess of that which was recorded for the control. This example illustrates that if a reservoir formulation has little to no inherent evaporation control designed within its composition then a reliance upon an external rate controlling method becomes imperaive if that reservoir formulation is to be consideredas suitable for use in a sustained delivery device. The technology disclosed herein extends the art by expanding the sources from which potentially suitable reservoir formulations might now be incorporated into these types of sustained delivery devices. The option of an expanded base from which to select a reservoir formulation also expands the potential to dispense volatile agents which heretofore might not have been suitable for dispensing from an erodible gel due to the lack of compatability which these agents might have with an aqueous based formulation or the lack of evaporative control formulated within such alternative reservoir compositions. The membranes as disclosed within provide for an external method of rate control which heretofore has been limited to some type of manually adjustable mechanical packaging design.

Figure 3:
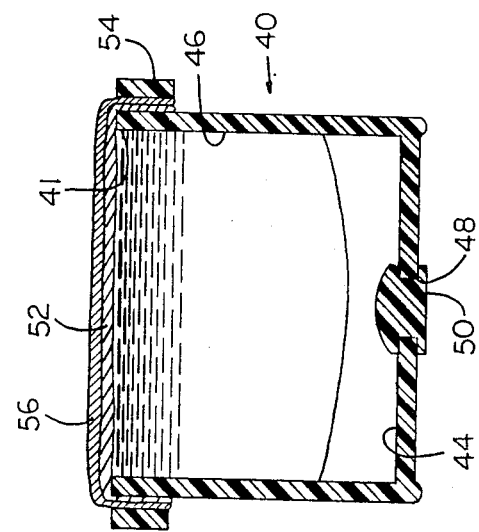
FIG. 3 is a side elevational view, in cross section illustrating an alternative form of membrane member part of an air treating device made in accordance with the present invention.

The preferred embodiment of this invention has been described above wherein the membrane material, prevents substantial penetration of the liquid gel through the membrane while still permitting sufficient penetration for physical bonding of the solidified gel to the membrane. If desired, a separatelayer of fibers which are readily wettable by the liquid gelling agent can be provided adjacent the gel supply to improve physical bonding thereto without detracting from the evaporation rate controlling function of the bulk of the main membrane material. In yet another embodiment of the invention as shown in FIG. 3, the evaporation rate controlling membrane may coprise a composite material with several layers, with the layer 52 nearest the gel being formed of a material wettable by the liquid gelling agent, while the layer or layers 56 further removed from the region penetrated by the liquid gel being non-wettable yet intimately in contact with said gel and serving only as a rate-controllng member over evaporation.

It should be understood that changes and modifications in the form, construction, arrangement and combination of the several parts of this assembly may be made and substituted for those shown herein and described without departing from the nature and principles of this invention. For example, as shown in FIG. 4, evaporation rate controlling membrane 60 may be selected solely for its evaporation rate controlling properties and without regard to the capacity of the membrane 60 also to prevent complete penetration and thus loss of the liquid gelling agent. In such embodiment a separate, a liquid gel solution impervious layer such as an aluminum foil sheet 62 will be provided over membrane layer 60 to stop any loss of the heated aqueous solution of liquid gelling agent that otherwise might flow through membrane 60. Suitable means such as a tab or a drawstring 64 may be provided for assisting the removal of a portion of the foil sheet 62 to activate the unit. Alternatively, a removable cap may be provided in place of sheet 62 to stop any loss of heated aqueous solution of liquid gelling agent during the filling operation.

Due to the macroporous nature of the membranes described herein and their capacity to permit the passage of air, the equilibration of pressure inside the container generally can be effected without special venting. This is achieved due to the slight amount of shrinkage in the diameter dimension of the gel which exposes a small portion of the membrane from the inside of the container and thus allows vacuum relief within the container.

The present invention has been described in connection with the dispersing of air freshening materials. However, the invention is not so limited, and may be advantageously employed for dispensing insecticides, germicides, fungicides, medicines or other desired volatile air-treating materials. Still other changes will be obvious to those skilled in the art.

I claim:

1. A reservoir air treating device comprising a container having vapor impermeable walls and an opening with an evaporation rate controlling membrane extending across said opening, and an erodible aqueous gel containing a volatile active ingredient cast onto said rate controlling membrane, said membrane permitting only a limited penetration by the gel in the liquid state but being sufficiently permeable to said liquid gel to establish physical attachment between the solidified gel and the membrane, which will support the entire weight of the cast gel, said membrane being sufficient permeable to the components of the aqueous solution comprising said gel and containing said active ingredient so as to permit co-evaporation of the active ingredient from the surface of said membrane.

2. The device of claim 1 wherein the membrane comprises a cellulosic fibrous membrane whose fibers are coated with a hydrophobic substance.

3. The device of claim 2 wherein the membrane comprises normally hydrophilic cellulose fibers having a silicone coating.

4. The device of claim 3 wherein the silicone is a polysiloxane.

5. The device of claim 4 wherein the silicone coating comprises a polydimethylsiloxane.

6. The device of claim 1 wherein the membrane comprises a normally hydrophilic porous membrane having a hydrophobic surface coating.

7. The device of claim 1 wherein the membrane comprises a non-woven synthetic textile bonded by a water retarding binder material.

8. The device of claim 1 wherein the membrane comprises a porous plastic material having a predetermined pore size and void volume.

9. The device of claim 8 wherein the membrane is selected from porous polyethylene and porous polypropylene.

10. The device of claim 1 wherein the membrane comprises a foamed polymeric material having a predetermined void volume and pore size.

11. The device of claim 10 wherein said foamed polymeric material is selected from the group consisting of a porous polyether, a porous polyester, a porous polyurethane and a porous polyvinyl alcohol formal foam material.

12. The device of claim 1 wherein said membrane compries a felted fabric having the weight of at least two ounces per square yard.

13. The device of claim 1 wherein said active agent is selected from the group consisting of a pheromone, a hormone, a fragrance, an insecticide, an insect attractant, a pharmaceutical agent, a veterinary drug and mixtures thereof.

14. The device of claim 1 wherein said active agent comprises one or a mixture of fragrances.

15. A reservoir air treating device comprising a container having vapor impermeable walls and an opening with an evaporation rate controlling membrane extending across said opening, and an erodible aqueous gel containing a volatile active ingredient cast onto said rate controlling membrane, the major portion of said membrane permitting only a limited penetration by an aqueous solution of liquefied gel but being sufficiently permeable to said liquid gel to establish a physical attachment between the solidified gel and the membrane, which will support the entire weight of the cast gel, said membrane sufficiently permeable to the components of the aqueous solution comprising said gel and containing said active ingredient so as to permit co-evaporation of the active ingredient from the surface of said membrane.

16. A reservoir air treating device according to claim 15, wherein said active agent is selected from the group consisting of a pherome, a hormone, a fragrance, an insecticide, an insect attractant, a pharmaceutical agent, a veterinary drug and mixtures thereof.

17. A reservoir air treating device according to claim 15, wherein said active agent comprises one or a mixture of fragrances.

18. The device of claim 15 wherein the membrane comprises a cellulosic fibrous membranea whose fibers are coated with a hydrophobic substance.

19. The device of claim 18 wherein the membrane comprises normally hydrophilic cellulose fibers having a silicone coating.

20. The device of claim 19 wherein the silicone is a polysiloxane.

21. The device of claim 20 wherein the silicone coating comprises a polydimethylsiloxane.

22. The device of claim 15 wherein the membrane comprises a normally hydrophilic porous membrane having a hydrophobic surface coating.

23. The device of claim 15 wherein the membrane comprises a non-woven synthetic textile bonded by a water retarding binder material.

24. The device of claim 15 wherein the membrane comprises a porous plastic material having a predetermined pore size and void volume.

25. The device of claim 15, wherein the membrane is selected from porous polyethylene and porous polypropylene.

26. The device of claim 15 wherein the membrane comprises a foamed polymeric material having a predetermined void volume and pore size.

27. The device of claim 15 wherein said foamed polymeric material is selected from the group consisting of a porous polyether, a porous polyester, a porous polyurethane and a porous polyvinyl alcohol formal foam material.

28. The device of claim 15 wherein said membrane comprises a felted fabrice having the weight of at least two ounces per square yard.

29. A reservoir air treating device comprising a container having vapor impermeable walls and an opening with an evaporation rate controlling membrane extendingacross said opening, and an erodible aqueous gel containing an active agent cast onto said rate controlling membrane, said membrane being essentially non-wetted by water in a standard wicking test after 3 minutes but being sufficiently permeable to the liquefied gel to establish physical attachment between the solidified gel and the membrane, which will support the entire weight of the cast gel, said membrane being essentially non-wicking to water while being sufficiently permeable to the components of the aqueous solution comprising said gel and containing said active ingredient so as to permit co-evaporation of the active ingredient from the surface of said membrane.

30. A reservoir air treating device according to claim 29 wherein said active agent is selected from the group consisting of a pheromone, a hormone, a fragrance, an insecticide, an insect attractant, a pharmaceutical agent, a veterinary drug and mixtures thereof.

31. A reservoir air treating device comprising a container having vapor impermeable walls and an opening with an evaporation rate controlling membrane extending across said opening, and an erodible aqueous gel containing a volatile active ingredient cast ont said rate controlling membrane, said membrane being sufficiently permeable to the liquefied gel to establish physical attachment between the solidified gel and the membrane, which will supportthe entire weight of the cast gel, and including an external means for containing the liquefied gel within the container until the gel sets at least in part, said membrane being sufficiently permeable to the components of the aqueous solution comprising said gel and containing said active ingredient to permit co-evaporation of the active ingredient from the surface of said membrane.

32. The device of claim 31 wherein means for containing the liquid gel comprises a liquid impervious member disposed to the outside of said porous membrane.

33. The device of claim 31 wherein said active agent is selected from the group consisting of a pheromone, a hormone, a fragrance, an insecticide, an insect attractant, a pharmaceutical agent, a veterinary drug and mixtures thereof.

34. The device of claim 31 wherein said active agent comprises one or a mixture of fragrances.

35. The device of claim 31 wherein the membrane comprises a porous plastic material having a predetermined pore size and void volume.

36. The device of claim 31 wherein the membrane is selected from porous polyethylene and porous polypropylene.

37. The device of claim 31 wherein the membrane comprises a foamed polymeric material having a predetermined void volume and pore size.

38. The device of claim 31 wherein said foamed polymeric material is selected from the group consisting of a porous polyether, a porous polyester, a porous polyurethane and a porous polyvinyl alcohol formal foam material.

39. The device of claim 31 wherein said membrane comprises a felted fabric having the weight of at least two ounces per square yard.

40. The device of claim 1 wherein the membrane comprises a composite material formed of at least two layers, at last one of said layers being wettable by the liquefied gel, and at least one other of said layers serving as an evaporation rate-controlling member.

41. The device of claim 15 wherein the membrane comprises a composite material formed of at least two layers, at last one of said layerss being wettable by the liquefied gel, and at least one other of said layers serving as an evaporation rate-controlling member.

42. The device of claim 29 wherein the membrane comprises 1 composite material formed of at least two layers, at least one of said layers being wettable by the liquefied gel, and at least one other of said layers serving as an evaporation rate-controlling member.

43. The device of claim 31 wherein the membrane comprises a composite material formed of at least two layers, at least one of said layers being wettable by the liquefied gel, and at least one other of said layers serving as an evaporation rate-controlling member.

44. The device of claim 1 wherein said membrane is essentially non-wicking to water.

45. The device of claim 15 wherein said membrane is essentially non-wicking to water.

* * * * *

UNITED STATES PATENT AND TRADEMARK OFFICE
CERTIFICATE OF CORRECTION

PATENT NO. : 4,809,912
DATED : March 7, 1989
INVENTOR(S) : Thomas F. SANTINI

It is certified that error appears in the above—identified patent and that said Letters Patent is hereby corrected as shown below:

Claim 18, line 60, "membranea" should be --membrane--.

Claim 28, line 22, "fabrice" should be --fabric--.

Claim 29, line 27, "dingacross" should be --ding across--.

Claim 31, line 50, "ont" should be --onto--.

Claim 31, line 55, "supportthe" should be --support the--.

Claim 37, line 11, "31wherein" should be --31 wherein.

Claim 40, line 3, "last" should be --least--.

Claim 41, line 6, "last" should be --least--.

Claim 41, line 6, "layerss" should be --layers--.

Signed and Sealed this

Twenty-second Day of August, 1989

Attest:

DONALD J. QUIGG

Attesting Officer

Commissioner of Patents and Trademarks